(12) United States Patent
Mihlin et al.

(10) Patent No.: US 11,058,371 B2
(45) Date of Patent: *Jul. 13, 2021

(54) SIMULTANEOUS ATTENUATION AND ACTIVITY RECONSTRUCTION FOR POSITRON EMISSION TOMOGRAPHY

(71) Applicant: The Board of Trustees of the Leland Stanford Junior University, Palo Alto, CA (US)

(72) Inventors: Alexander Mihlin, Stanford, CA (US); Craig S. Levin, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 1832 days.

This patent is subject to a terminal disclaimer.

(21) Appl. No.: 14/528,631

(22) Filed: Oct. 30, 2014

(65) Prior Publication Data
US 2015/0119694 A1   Apr. 30, 2015

Related U.S. Application Data

(60) Provisional application No. 61/897,294, filed on Oct. 30, 2013.

(51) Int. Cl.
*G01T 1/29*        (2006.01)
*A61B 6/03*        (2006.01)
(Continued)

(52) U.S. Cl.
CPC ............ *A61B 6/037* (2013.01); *A61B 6/5205* (2013.01); *G01R 33/481* (2013.01);
(Continued)

(58) Field of Classification Search
CPC ................ G01R 33/481; G06T 11/006; G06T 2211/424; A61B 6/5205; A61B 6/037; A61B 5/0035; A61B 5/055
See application file for complete search history.

(56) References Cited

U.S. PATENT DOCUMENTS

| | | | | |
|---|---|---|---|---|
| 2006/0163485 A1* | 7/2006 | Stearns | ................. | G01T 1/2985 250/363.03 |
| 2011/0303835 A1* | 12/2011 | Fenchel | ................. | A61B 6/037 250/252.1 |
| 2014/0158890 A1* | 6/2014 | Pistorius | ............... | G01T 1/1647 250/362 |

FOREIGN PATENT DOCUMENTS

| | | | | |
|---|---|---|---|---|
| WO | WO 2013/164731 | * | 11/2013 | ............... G01T 1/29 |
| WO | WO 2013/164731 | * | 12/2013 | ............... A61B 6/03 |

OTHER PUBLICATIONS

Krol, An EM Algorithm for Estimating SPECT Emission and Transmission Parameters from Emission Data Only, IEEE Transactions on Medical Imaging, vol. 20, No. 3, Mar. 2001.*

(Continued)

*Primary Examiner* — James M Kish
(74) *Attorney, Agent, or Firm* — Lumen Patent Firm

(57) ABSTRACT

A method of PET image reconstruction is provided that includes obtaining intra-patient tissue activity distribution and photon attenuation map data using a PET/MRI scanner, and implementing a Maximum Likelihood Expectation Maximization (MLEM) method in conjunction with a specific set of latent random variables, using an appropriately programmed computer and graphics processing unit, wherein the set of latent random variables comprises the numbers of photon pairs emitted from an electron-positron annihilation inside a voxel that arrive into two given voxels along a Line of Response (LOR), where the set of latent random variables results in a separable joint emission activity and a photon attenuation distribution likelihood function.

2 Claims, 13 Drawing Sheets

(51) Int. Cl.
- *G01R 33/48* (2006.01)
- *A61B 6/00* (2006.01)
- *G06T 11/00* (2006.01)
- *A61B 5/00* (2006.01)
- *A61B 5/055* (2006.01)

(52) U.S. Cl.
CPC .......... G01T 1/2985 (2013.01); G06T 11/006 (2013.01); *A61B 5/0035* (2013.01); *A61B 5/055* (2013.01); *G06T 2211/424* (2013.01)

(56) References Cited

OTHER PUBLICATIONS

Pierro et al., "Simultaneous Activity Attenuation Reconstruction in Positron Emission Tomography Via Maximum Likelihood and Iterative Methods", 2005 IEEE, pp. 1-4. (Year: 2005).*

Pierro, Alvaro. "A Modified Expectation Maximization Algorithm for Penalized Likelihood Estimation in Emission Tomography"; IEEE Transactions on Medical Imaging, vol. 14, No. 1, Mar. 1995. pp. 132-137. (Year: 1995).*

Rezaei et al., "Simultaneous Reconstruction of Activity and Attenuation in Time-of-Flight PET"; IEEE Transactions on Medical Imaging, vol. 31, No. 12, Dec. 2012. pp. 2224-2233. (Year: 2012).*

Prince et al., "Medical Imaging Signals and Systems"; Textbook. 2005, Pearson. <15 pages total> Includes Cover Page illustrating date, pp. 2-10 (textbook pp. vii-xiv) showing Table of Contents, pp. 11-36 (textbook pp. 286-311) showing Chapter 9. (Year: 2005).*

Salomon, A. Goedicke, B. Schweizer, T. Aach, and V. Schulz. Simultaneous reconstruction of activity and attenuation for pet/mr. Medical Imaging, IEEE Trans-actions on, 30(3):804-813, 2011.

Nuyts, et al. Simultaneous maximum a posteriori reconstruction of attenuation and activity distributions from emission sinograms. Medical Imaging, IEEE Transactions on, 18(5):393-403, 1999.

De Pierro and F. Crepaldi. Activity and attenuation recovery from activity data only in emission computed tomography. Computational and Applied Mathematics, 25:205-227, 2006.

Conti, I. Hong, and C. Michel. Reconstruction of scattered and unscattered pet coincidences using tof and energy information. Physics in Medicine and Biology, 57(15):N307-N317, 2012.

Cade et al. Attenuation map estimation without transmis-sion scanning using measured scatter data. In Nuclear Science Symposium and Medical Imaging Conference (NSS/MIC), 2011 IEEE, pp. 2657-2663, 2011.

Lange and R. Carson. Em reconstruction algorithm for emission and transmission tomography. J. Comput. Assist. Tomogr., 8:306-316, 1984.

Shepp et al. Maximum likelihood re-construction for emission tomography. Medical Imaging, IEEE Transactions on, 1(2):113-122, 1982.

* cited by examiner

New latent variables - $X_{jk}^{di}$
Separable likelihood function $\propto P(X_{jk+1}^{di} | X_{jk}^{di}) \propto P(\mu_k)$
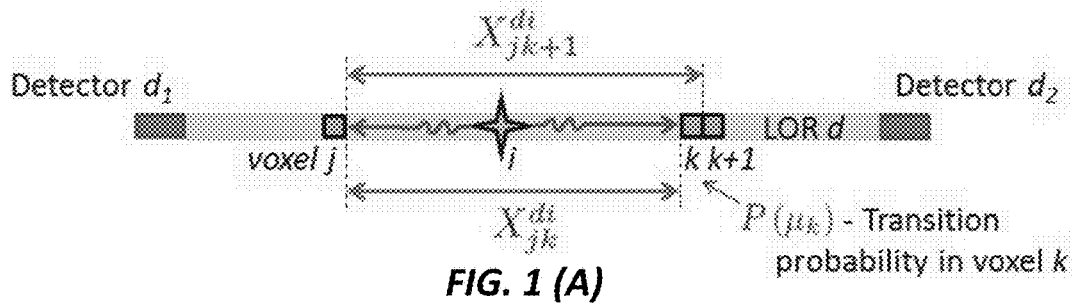
FIG. 1 (A)
Canonical latent variables - $X_{d_1 d_2}^{di}$
Non-Separable likelihood function $\propto P(X_{d_1 d_2}^{di}) \propto e^{-\prod_{k \in \Gamma_d} P(\mu_k)}$
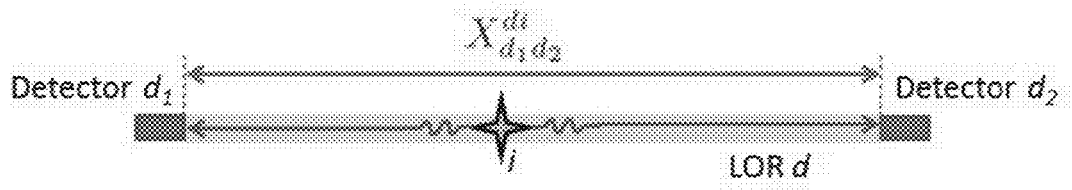
$X_{jk}^{di}$ - number of photon pairs reaching voxels $j$ and $k$ along LOR $d$, after being emitted in voxel $i$
FIG. 1 (B) Prior Art

SIMULTANEOUS ATTENUATION AND ACTIVITY RECONSTRUCTION FOR POSITRON EMISSION TOMOGRAPHY

CROSS-REFERENCE TO RELATED APPLICATIONS

This application claims priority from U.S. Provisional Patent Application 61/897,294 filed Oct. 30, 2013, which is incorporated herein by reference.

FIELD OF THE INVENTION

The present invention relates generally to Positron Emission Tomography (PET). More particularly, the invention relates to a method of PET image reconstruction by obtaining intra-patient tissue activity distribution and photon attenuation map and implementing a Maximum Likelihood Expectation Maximization (MLEM) method.

BACKGROUND OF THE INVENTION

Quantitative Positron Emission Tomography (PET) requires the knowledge of the intra-patient photon attenuation map. This attenuation map may be obtained via a priori transmission scan. However, a transmission scan exposes the patient to additional ionizing radiation, prolongs the overall scan time and requires dedicated equipment. Moreover, such transmission scan is unavailable in combined PET and Magnetic Resonance Imaging (PET/MRI) scanners. To avoid these shortcomings, several groups proposed obtaining the attenuation map from the PET emission data alone.

Furthermore, PET image reconstruction assumes "true" coincidences, where both photons originate from the same radionuclide decay and do not scatter inside the tissue. Thus, in many cases over half of the detected coincidences are discarded, rather than used in the reconstruction process. Moreover, around 60% of such discarded coincidences have a rather simple structure, comprising just a single tissue scattered photon. Some recent work targeted the incorporation of such simple structured coincidences into activity reconstruction in PET and into activity and attenuation reconstruction in Single Photon Emission Tomography (SPECT).

What is needed is a method of reconstructing the intra-patient tissue activity distribution and photon attenuation map, using true- and tissue scattered coincidences using the Maximum Likelihood Expectation Maximization (MLEM) method in conjunction with a new set of latent random variables.

SUMMARY OF THE INVENTION

To address the needs in the art, a method of PET image reconstruction is provided that includes obtaining intra-patient tissue activity distribution and photon attenuation map using a PET/MRI scanner, and implementing a Maximum Likelihood Expectation Maximization (MLEM) method in conjunction with a specific set of latent random variables, using an appropriately programmed computer and graphics processing units, wherein the set of latent random variables comprises the numbers of photon pairs emitted from an electron-positron annihilation inside a voxel that arrive into two given voxels along a Line of Response (LOR), where the set of latent random variables results in a separable joint emission activity and a photon attenuation distribution likelihood function.

According to one aspect, the invention further comprises incorporating Time of Flight (TOF) data and Magnetic Resonance Imaging (MRI) data to the MLEM method, where detector scatter with partial energy deposition that creates a degeneracy for the identification of tissue scattered coincidences is accounted for by (i) setting an appropriate low energy threshold for data acquisition, or (ii) incorporating the detector scatter events into the MLEM method, or (i) and (ii).

According to another aspect, the invention further comprises incorporating Single Scatter Approximation (SSA) that defines tissue scatter coincidences as events where only one of the two photons is scattered and is scattered only once, wherein the tissue scatter coincidence affects attenuation coefficients of the photon defined by a distribution of possible scatter points forming a hollow shell-shape in the detector's field of view and the emission activity coefficients inside a corresponding solid shell.

BRIEF DESCRIPTION OF THE DRAWINGS

FIGS. 1a-1b show a comparison between the likelihood functions obtained with the current invention and canonical latent variables, where the latent variables (1a) yield a separable likelihood function, in contrast with the non {separable likelihood function (1b) obtained with the prior art canonical latent variables.

DETAILED DESCRIPTION

The current invention provides a method of reconstructing the intra-patient tissue activity distribution and photon attenuation map, using true- and tissue scattered coincidences. To that end, the Maximum Likelihood Expectation Maximization (MLEM) method is employed in conjunction with a new set of latent random variables.

The method according to the current invention has some advantages: (i) It results in a separable activity distribution and photon attenuation map likelihood function, which simplifies maximization (FIG. 1). (ii) It substantially increases the number of useful coincidences. (iii) It allows for a parallel reconstruction at the cost of a modest increase in computational complexity.

The log-likelihood maximization procedure poses a computational challenge, due to the non-separability of the joint tissue activity distribution, and photon attenuation map-likelihood function. Some researchers proposed to address this challenge by maximizing the log-likelihood via the Gradient Ascent or the Newton-Raphson methods.

However, a similar challenge for CT and SPECT was addressed differently by obtaining a separable likelihood function using an alternative set of latent random variables. The method according to the current invention extends the previous work for PET and incorporates the use of some of the tissue scattered coincidences. It results in a separable likelihood function, which is easier to maximize than a non-separable likelihood function.

Another challenge with PET image reconstruction is the measurement errors. These errors propagate into the reconstruction process, due to the coupling between the observables and reconstructed parameters. This error propagation may be addressed via the use of Time of Flight (TOF) data, which decouples some of the parameters and observables. However, error propagation is particularly challenging for the use of tissue scattered coincidences. This is due to the large number of voxels directly affected by a tissue scattered coincidence, compared with a smaller number of voxels directly affected by a true coincidence (grey line in FIG. 2). The method according to the current invention addresses this challenge in two ways: (i) if available, TOF data is incorporated into the statistical model and (ii) some of the parameters and observables are decoupled via the Single Scatter Approximation (SSA). This approximation assumes that only one of the two coincidence photons scatters in the subject and it scatters only once. Using this assumption, each scattered coincidence affects the attenuation coefficients as described by a distribution of possible scatter points forming a hollow "shell", rather than a solid "football", in the field of view.

Figure 3:
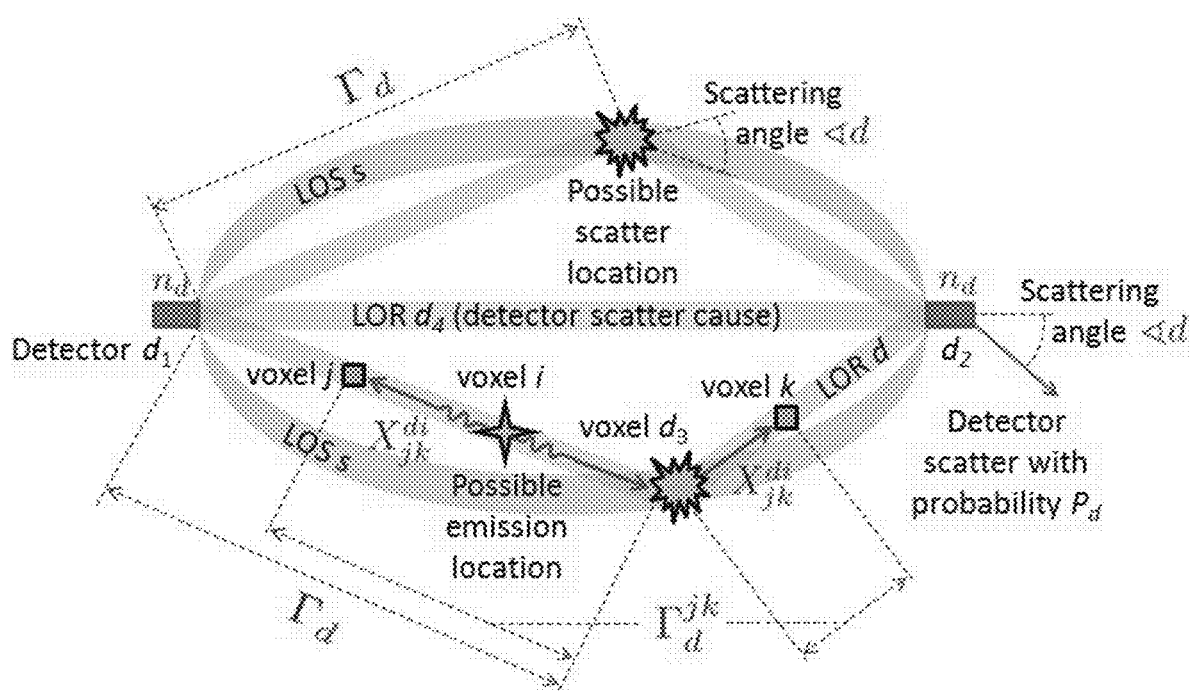
FIG. 3 shows a scattered coincidence, where a two dimensional cross section of the three dimensional Loci of Scatter (LOS) is shown as an elliptical shape, where some of the corresponding LORs are shown by the broken grey tubes and detector scatter occurs with probability $P_d$, and is due to the photons emitted along LOR $d_4$, (straight grey tube), and $\Gamma_d$ comprises the LOR segments where emission could have taken place, and $\Gamma_d^{jk}$ coincides with the corresponding LOR segments between voxels j and k, according to the current invention.

A further challenge with the use of tissue scattered coincidences, is detector scatter with partial energy deposition (see FIG. 3). Such scatter creates degeneracy for the identification of tissue scattered coincidences. The current method addresses this challenge in two ways: (i) such detector scatter is incorporated into the statistical model and (ii) a method is proposed for setting the low energy data acquisition threshold. This threshold helps filter out some of the detector scatter.

Furthermore, the current invention allows for the incorporation of a priori information, with no further coupling of the update equations. For instance, such information regarding the photon attenuation map may be obtained via a priori Magnetic Resonance Imaging (MRI) scan, available in combined PET/MRI scanners.

In summary, the current invention is a method for a joint PET reconstruction of the intra-patient tissue activity distribution and photon attenuation map, and represents the first method which results in a separable joint activity and attenuation map likelihood function for PET.

According to the invention, the three-dimensional field of view is divided into voxels.

Figure 2:
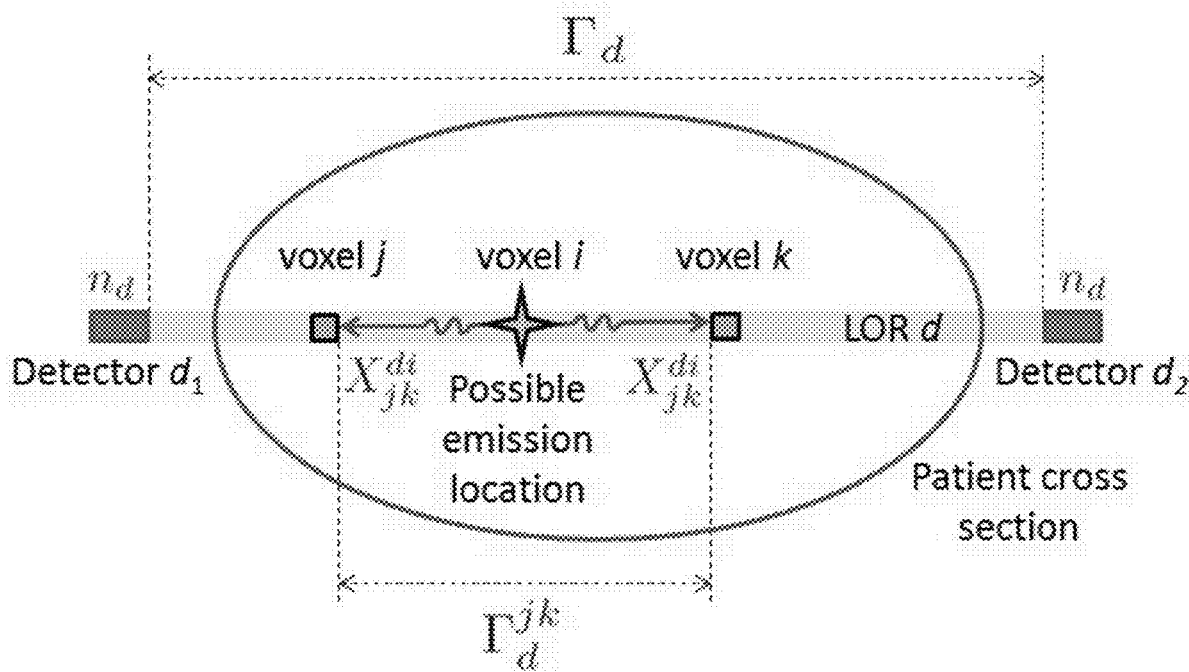
FIG. 2 shows a true coincidence with LOR d is denoted by the light-grey tube, where the parameters $X_{jk}^{di}$ denote the numbers of photon pairs reaching voxels j and k along LOR d, after being emitted inside voxel I, and $n_d$ denotes the total number of detected coincidence pairs. $\Gamma_d$ coincides with LOR d, and $\Gamma_d^{jk}$ coincides with the LOR segment between voxels j and k, according to the current invention.

The model incorporates "true" and "scattered" coincidences. As illustrated in FIG. 2, a true coincidence is comprised of two non-scattered photons. FIG. 3 shows a tissue-scatted coincidence. A coincidence is denoted "scattered" when only one of its photons scattered in tissue and it is scattered only once.

As shown in FIG. 2, a true coincidence is characterized by a Line of Response (LOR) (grey line). A LOR denotes the set of all possible emission locations, such that the two coincidence photons follow a given path.

Particularly, a "true" LOR has the form of a straight tube. As shown in FIG. 3, a scattered coincidence is characterized by the set of possible scatter locations, which are denoted as "Loci of Scatter" (LOS) (oval grey curve). The LOS have the form of a spherical shell, the width of which is determined by the PET scanner's energy resolution. The possible paths of the scattered coincidence photons are characterized by a LOR set, as opposed to a single LOR. Such LORs have the form of tubes broken at the LOS shell (broken grey lines in FIG. 3). As shown in the figure, a LOS is defined by a detector pair and a scattering angle. Hence, the expression $$\text{LOR } d \in \text{LOS } s \quad (1)$$

indicates that LOR d and LOS s correspond to the same detector pair and scattering angle. Particularly, several LORs may contribute to the same observed coincidence number $n_d$:

$$d, d' \in \text{LOS } s \Rightarrow n_d = n_{d'} \quad (2)$$

The model contains observed and latent variables, shown in FIGS. 2 and 3. The observed variables are comprised of the vector, $n \equiv \{n_d\}$, of true and scattered coincidences, where d is a LOR index. The latent variables, $X_{jk}^{di}$, are comprised of a subset of the numbers of photon pairs reaching voxels j and k along LOR d, after being emitted in voxel i. Particularly, $X_{ii}^{di}$ denotes the total number of photons emitted from voxel i into LOR d. The observables, n, are completely determined by the variables $X_{jk}^{di}$ via the following relation:

$$n_d = \sum_{i \in \Gamma_d} X_{d_1 d_2}^{di} \quad (3)$$

where $d_1$ and $d_2$ denote the indices of the two detectors associated with LOR d. The symbol $\Gamma_d$ denotes the set of possible emission locations along LOR d. As illustrated in FIG. 2, for a true coincidence, $\Gamma_d$ coincides with the LOR volume. However, as illustrated in FIG. 3, this is not the case for a scattered coincidence. In this case, $\Gamma_d$ coincides with the segments of the many LORs related to a mutual LOS, between the detector where the non-scattered photon was observed and the LOS outer surface. The symbol $\Gamma_d^{jk}$ denotes the section of LOR d between voxels j and k.

Figure 4:
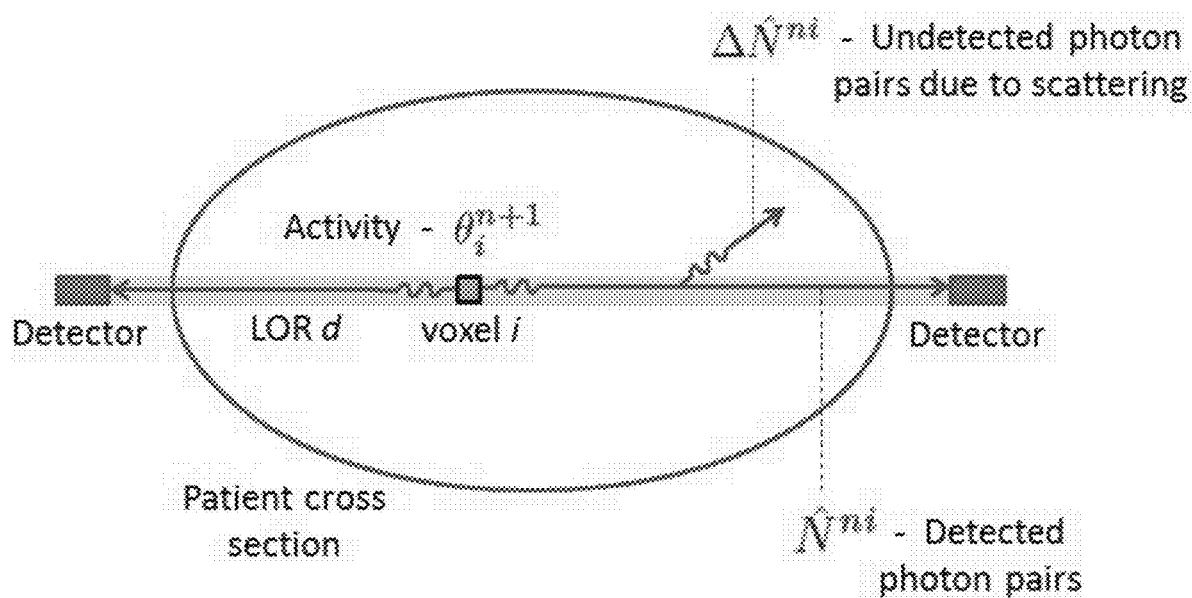
FIG. 4 shows the parameters used in the nth-iteration tissue activity distribution update equation (4), where the parameters $\hat{N}^{mi}$ and $\Delta\hat{N}^{mi}$ denote respectively the mean number of detected and attenuated photon pairs, emitted inside voxel i.

The model parameters are the activity distribution, $\theta_i$, and the attenuation coefficients, $\mu_i$, per voxel i. The activity is defined as the mean number of intra-voxel annihilations. An attenuation coefficient is defined as the intra-voxel photon scattering cross section. These parameters are determined via the MLEM method. In this method, the likelihood function is maximized by an iterative solution of a set of update equations. As derived below and shown in FIG. 4, the nth-iteration activity update equation is given by the following expression:

$$\theta_i^{n+1} = \frac{1}{P_i}(\hat{N}^{ni} + \Delta \hat{N}^{ni}) \quad (4)$$

where $\hat{N}^{ni}$ and $\Delta \hat{N}^{ni}$ are, respectively, the mean number of detected and attenuated photon pairs, emitted from voxel i. In the absence of attenuation, $P_i$ is the total detection probability of a photon pair emitted in voxel i. It depends on the scanner's geometry and on its specifications, such as the detector's quantum efficiencies.

Figure 5:
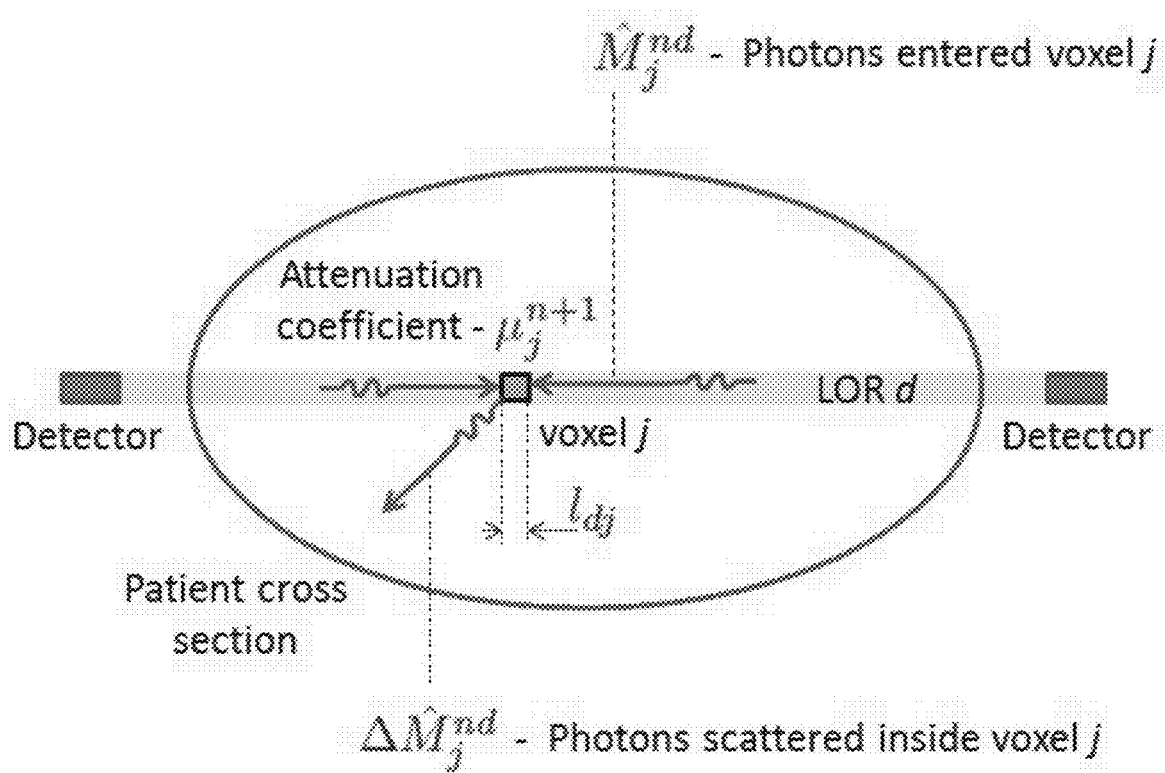
FIG. 5 shows the parameters used in the nth-iteration photon attenuation map update equation (5), where the parameters $\hat{M}_j^{nd}$ and $\Delta\hat{M}_j^{nd}$ denote the mean numbers of a subset of the photons emitted into LOR d, which respectively traversed- and scattered inside-voxel j, where the photon attenuation coefficient in a particular voxel is proportional to the ratio between the photons scattered inside- and incident into-this voxel, where the number of fore-projections required for the calculation of $\hat{M}_j^{nd}$ and $\Delta\hat{M}_j^{nd}$ may be reduced by considering only a subset of the incident photons, as opposed to the complete photon set emitted from all the voxels, according to the current invention.

As derived below and shown in FIG. 5, the update equation for the attenuation coefficients is given by the following expression:

$$\sum_d r_{dj} \left[ \frac{1}{e^{\mu_j^{n+1} r_{dj}} - 1} \Delta \hat{M}_j^{nd} - \Delta \hat{M}_j^{nd} \right] = 0 \quad (5)$$

where d indicates only the observed LORs, as opposed to all possible LORs. The parameters $\hat{M}_j^{nd}$ and $\Delta \hat{M}_j^{nd}$ are the expected cardinality of a subset of the photons emitted into LOR d, which respectively traversed- and scattered inside-voxel j. The parameter $r_{dj}$ is defined as follows:

$$r_{dj} = \begin{cases} l_{dj} & d \in \text{LOR} \\ \dfrac{P_{KN}(\sphericalangle d)\Omega_d l_{dd_3}}{\int P_{KN}(\alpha) d\alpha} & d \in \text{LOS} \end{cases} \quad (6)$$

where, as shown in FIG. 5, $l_{dj}$ denotes the intersection length between LOR d and voxel j. $P_{KN}$ is the Klein-Nishina scattering cross section, $\sphericalangle d$ is the scattering angle (see FIG. 3) and d is the solid angle between the scattering location and the downstream detector. As shown in FIG. 3, the index $d_3$ denotes the voxel containing the possible scattering location along LOR d. In a mean field approximation, with $r_{dj} \approx r_j$, the attenuation coefficient update rule is given by $$\mu_j^{n+1} r_j \approx -\ln \left[ \frac{\sum_d \hat{M}_j^{nd}}{\sum_d (\hat{M}_j^{nd} + \Delta \hat{M}_j^{nd})} \right] \quad (7)$$

$$\approx \frac{\sum_d \Delta \hat{M}_j^{nd}}{\sum_d (\hat{M}_j^{nd} + \Delta \hat{M}_j^{nd})}$$

where the second line holds for small attenuation, when $\Delta M_k^{nd} \ll M_k^{nd}$. Since Eq. (5) is monotonic in $\mu_j^{n+1}$, it has a unique solution. Since for small voxels, $\mu_j r_{dj}$ is also small, Eq. (5) may be approximated via the following Taylor series expansion:

$$\frac{x}{e^x - 1} \approx 1 - \frac{x}{2} + \frac{x^2}{12} + O(x^3) \quad (8)$$

Moreover, since for x>0, $$1 - \frac{x}{2} \le \frac{x}{e^x - 1} \le 1 \quad (9)$$

the exact solution is bounded by $$\frac{\sum_d \Delta \hat{M}_j^{nd}}{\sum_d r_{dj} \hat{M}_j^{nd}} \le \mu_j^{n+1} \le \frac{\sum_d \Delta \hat{M}_j^{nd}}{\sum_d r_{dj} \left( \hat{M}_j^{nd} + \frac{1}{2} \Delta \hat{M}_j^{nd} \right)} \quad (10)$$

The use of the first order expansion from Eq. (8), results in the following update rule for the attenuation coefficients:

$$\mu_j^{n+1} = \frac{\sum_d \Delta \hat{M}_j^{nd}}{\sum_d r_{dj}\left(\hat{M}_j^{nd} + \frac{1}{2}\Delta \hat{M}_j^{nd}\right)} \quad (11)$$

It was found that for such first order expansion, the SPECT likelihood begins to decrease after about 100 iterations, following an initial increase. To address this issue, a second order expansion is used, which results in a quadratic equation in $\mu_j^{n+1}$. This approximate solution and the bounds on the exact solution from Eq. (10), may be farther refined via a higher order Taylor series expansion. Moreover, since the attenuation coefficient update equation (5) is one-dimensional, it may be solved numerically, using approaches, such as Ollingers' method.

Turning now to the model details, the following section provides sufficient details for the calculation of the model parameters defined above. Moreover, some supplementary derivations are given below. The reconstruction equations are summarized below.

The variables $\hat{N}^{ni}$, $\Delta\hat{N}^{ni}$ and $P_i$ from Eq. (4) (FIG. 4), are given by the following expressions:

$$\hat{N}^{ni} = \sum_d E(X_{d_1 d_2}^{di} \mid n_d) \quad (12)$$

$$\Delta \hat{N}^{ni} = \sum_d [E(X_{ii}^{di}) - E(X_{d_1 d_2}^{di})] \quad (13)$$

$$P_i = \frac{1}{\sum_{\forall d} c_{di}^t} \quad (14)$$

where the parameters $X_{jk}^{di}$ denote the numbers of photon pairs reaching voxels j and k along LOR d, after being emitted inside voxel i. The symbol $\forall d$ indicates all possible-, as opposed to just detected-, LORs. The parameters $c_{di}^t$ are given by the following expression:

$$c_{di}^t = c_{di} \begin{cases} 1 & \text{TOF data unavailable} \\ \mathcal{N}\left(\frac{tc}{2}, \sigma_d^2\right)\Big|_{r_{di}} & \text{TOF data available} \end{cases} \quad (15)$$

where, in the absence of attenuation, $c_{di}$ is the probability for an emitted photon pair to be detected in LOR d. Particularly, it accounts for the geometric effects and for the detector's quantum efficiencies. The symbol N denotes the Gaussian distribution. The parameter t denotes the TOF time difference. $\sigma_d$ is the standard deviation associated with the time resolutions of detectors $d_1$ and $d_2$. $r_{di}$ is the distance between the center of voxel i and the center of LOR d. The expectations of the parameters $X_{jk}^{di}$ are given by $$E(X_{jk}^{di}) \equiv \lambda_{jk}^{di} = \theta_i c_{di}^t \gamma_{jk}^d \quad (16)$$

$$E(X_{d_1 d_2}^{di} \mid n_d) = \frac{\lambda_{d_1 d_2}^{di} n_d}{\left(\sum_{j \in \Gamma_d} + P_d \sum_{j \in \Gamma_{d_A}}\right)\lambda_{d_1 d_2}^{dj}} \quad (17)$$

where $\gamma_{jk}^d$ denotes the probability for a photon pair emitted between voxels j and k along LOR d, reaching these voxels:

$$\gamma_{jk}^d = e^{-\sum_{i \in \Gamma_d^{jk} \backslash d_3} \mu_i r_{di}}\left(1 - e^{-\mu_{d_3} r_{dd_3}} I_{d_3 \in \Gamma_d^{jk}}\right) \quad (18)$$

and the symbol I denotes the indicator function. As discussed below, the second term in the denominator of the conditional expectation in Eq. (17), accounts for detector scatter with partial energy deposition. $P_d$ is the probability for exactly one photon of a coincidence pair emitted along LOR d, depositing part of its energy inside a detector. As shown in FIG. 3, the index $d_4$ denotes the true LOR corresponding to the scattered LOR d.

As also discussed below, the parameter $\Delta\hat{M}_j^{nd}$ from Eq. (5) is given by the following expression:

$$\Delta\hat{M}_j^{nd} = \sum_{i \in \Gamma_d}\left\{\begin{array}{l} I_{j \neq d_3}\left[\left(\hat{X}_{ji}^{di} - \hat{X}_{j-1 i}^{di}\right)I_{j \leq i} + \left(\hat{X}_{d_1 j}^{di} - \hat{X}_{d_1 j+1}^{di}\right)I_{j > i}\right] + \\ \delta_{j,d_3}\left[\hat{X}_{d_3 - 1 i}^{di} + I_{d_3 \leq i} + \hat{X}_{d_1 d_3 + 1}^{di} I_{d_3 > i}\right] \end{array}\right\} \quad (19)$$

where $\delta_{i,j}$ is the Kronecker delta, and the voxel indices increase monotonically towards detector $d_2$. The conditional expectations $\hat{X}_{jk}^{di}$ are derived below:

$$\hat{X}_{jk}^{di} \triangleq E(X_{jk}^{di} \mid n) = \lambda_{jk}^{di} + \sum_{s \in \mathcal{D}_{jk}^d}\left[E(X_{s_1 s_2}^{si} \mid n_s) - \lambda_{s_1 s_2}^{si}\right] \quad (20)$$

As discussed below, the symbol $\mathcal{D}_{jk}^d$ denotes the set of LORs containing the variable $X_{jk}^{di}$. As discussed below, the parameter $\hat{M}_j^{nd}$ from Eq. (5) is given by the following expression:

$$\hat{M}_j^{nd} = \sum_{i \in \Gamma_d}\left\{\begin{array}{l} I_{j \neq d_3}\left[\hat{X}_{j-1 i}^{di} I_{j \leq i} + \hat{X}_{d_1 j+1}^{di} I_{j > i}\right] + \\ \delta_{j,d_3}\left[\begin{array}{l}\left(\hat{X}_{d_3 i}^{di} - \hat{X}_{d_3 - 1 i}^{di}\right)I_{d_3 \leq i} + \\ \left(\hat{X}_{d_1 d_3}^{di} - \hat{X}_{d_1 d_3 + 1}^{di}\right)I_{d_3 > i}\end{array}\right] \end{array}\right\} \quad (21)$$

Figure 6:
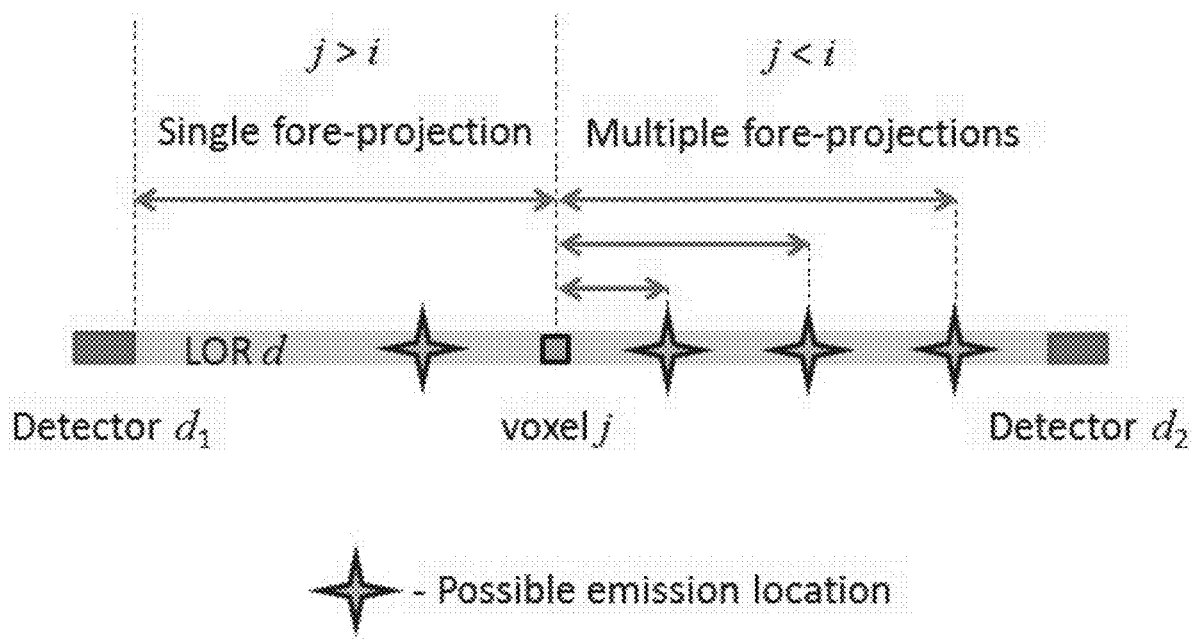
FIG. 6 shows the forward-projection values required for the calculation of $\hat{M}_j^{nd}$ and $\Delta\hat{M}_j^{nd}$, according to the current invention.

As shown in FIG. 6 and discussed below, the computation of $\Delta\hat{M}_j^{nd}$ and $\hat{M}_j^{nd}$ requires the calculation of multiple parameters $\gamma_{ji}^d$ for voxel indices j, i such that $$j, i \in \Gamma_d^{ji}, i > j \quad (22)$$

As described below, this computation may be accomplished incrementally with two projections.

As discussed below, if the scattering cross sections are sufficiently small, the Single Scatter Approximation may be applied. It may reduce noise propagation (see above) and accelerate the reconstruction process. In this approximation, $\gamma_{jk}^d$ from Eq. (18) simplifies into the following form:

$$\gamma_{jk}^d = \begin{cases} e^{-\sum_{i \in \Gamma_d^{jk}} \mu_i r_{di}} & d \in LOR \\ 1 - e^{-\mu_{d_3} r_{dd_3}} I_{j = d_1, k = d_2} & d \in LOS \end{cases} \quad (23)$$

Additionally, for scattered coincidences, $\Delta \hat{M}_j^{nd}$ and $\hat{M}_j^{nd}$ from Eqs. (19) and (21) respectively, are simplified into the following expressions:

$$\Delta \hat{M}_j^{nd} = \delta_{j,d_3} \sum_{i \in \Gamma_d} \hat{X}_{dd}^{di} \quad (24)$$

$$\hat{M}_j^{nd} = \delta_{j,d_3} \sum_{i \in \Gamma_d} (\hat{X}_{ii}^{di} - \hat{X}_{dd}^{di}) \quad (25)$$

In conclusion, the reconstruction algorithm is defined by Eqs. (4) and (11) in conjunction with Eqs. (12)-(21). The Single Scatter Approximation alters the attenuation reconstruction, as described by Eqs. (23)-(25). Particularly, the calculation of $\mu_j$ no longer involves all the LORs containing voxel j. Instead, it involves only the LORs corresponding to a photon scattering inside voxel j. Additionally, as described in Eqs. (24) and (25), a scattered LOR no longer involves the calculation of $\gamma_{jk}^d$ for various j and k, but only the calculation of $\gamma_{d_1 d_2}^d$. Moreover, as shown in Eq. (23), the calculation of $\gamma_{d_1 d_2}^{nd}$ no longer involves a forward-projection along LOR d, but is local.

Turning now to the implementation of the details, described herein is the method for the numerical calculation of the reconstruction update equations. Additionally, it references a Graphics Processing Units (GPU) based computing formulation, appropriate for the method according to the current invention. Further, discussed are the considerations in approximating the normalization parameter $P_i$. For simplicity, only true-, as opposed to scattered-, coincidences are treated here.

The reconstruction update equations, which were introduced above, are given by the following expressions:

$$\theta_i^{n+1} = \frac{\theta_i^n}{P_i} \sum_d c_{di}^t \left( \frac{n_d}{\sum_{j \in \Gamma_d} \theta_j^n c_{dj}^t} + 1 - \gamma_{d_1 d_2}^{nd} \right) \quad (26)$$

$$\mu_j^{n+1} = \frac{\sum_d (1 - e^{-\mu_j^n l_{dj}}) R_j^{nd}}{\sum_d l_{dj} [G^{nd} + (1 + e^{-\mu_j^n l_{dj}}) R_j^{nd} / 2]} \quad (27)$$

$$G^{nd} = n_d - \gamma_{d_1 d_2}^{nd} \sum_{i \in \Gamma_d} \theta_i^n c_{di}^t \quad (28)$$

$$R_j^{nd} = \sum_{i \in \Gamma_d} \theta_i^n c_{di}^t \gamma_{ji}^{nd} I_{i \geq j} + \gamma_{d_1 j}^{nd} \sum_{i \in \Gamma_d} \theta_i^n c_{di}^t \gamma_{ji}^{nd} I_{i < j} \quad (29)$$

where $G^{nd}$ denotes the difference between the detected- and expected-number of counts along LOR d, and $R_j^{nd}$ denotes the cardinality of a subset of the photons entering voxel j along LOR d. Notably, when $G^{nd} \ll R_j^{nd}$ and $\mu_j^n l_{dj} \ll 1$, Eq. (27) reduces into $\mu_j^{n+1} = \mu_j^n$, and the photon attenuation map reconstruction process converges. The computation of Eq. (26) requires a single forward- and back-projection. As described below, the computation of Eq. (27) requires two projections along each LOR. To that end, Eqs. (27)-(29) are formulated in terms of the following parameters:

$$S_j^d \triangleq \sum_{i \in \Gamma_d} \theta_i^n c_{di}^t \gamma_{ji}^{nd} I_{i \geq j} \quad (30)$$

$$\Delta_j^d \triangleq \sum_{i \in \Gamma_d} \mu_i^n l_{di} I_{i < j} \quad (31)$$

$$K_j^d \triangleq \sum_{i \in \Gamma_d} \theta_i^n c_{di}^t \gamma_{ji}^{nd} I_{i < j} \quad (32)$$

which results in the following expressions:

$$R_j^{nd} = \theta_j^n c_{dj}^t + S_{j+1}^d + e^{-\Delta_j^d} K_j \quad (33)$$

$$G^{nd} = n_d - e^{-\Delta_{d_2}^d} K_{d_2} \quad (34)$$

Figure 7:
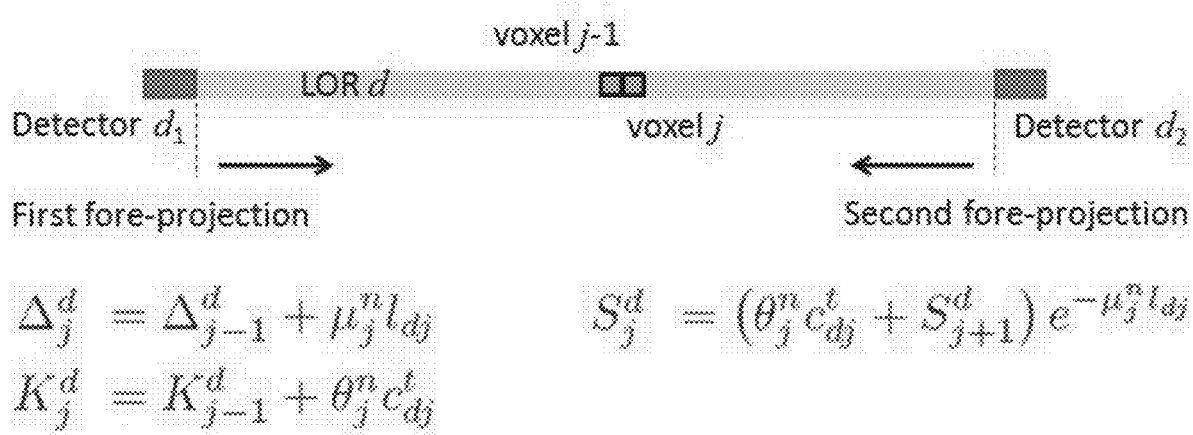
FIG. 7 shows an incremental calculation of the parameters $S_j^d$, $\Delta_j^d$ and $K_j^d$, which are required for the photon attenuation map update, where the parameters $\Delta_j^d$ and $K_j^d$ are calculated by a projection directed towards detector $d_2$, and the parameters $S_j^d$ are calculated by a second, oppositely directed, projection, according to the current invention.

As illustrated in FIG. 7, the parameters $S_j^d$, $\Delta_j^d$ and $K_j^d$ may be calculated incrementally, using the following relations:

$$S_j^d = (\theta_j^n c_{dj}^t + S_{j+1}^d) e^{-\mu_j^n l_{dj}} \quad (35)$$

$$\Delta_j^d = \Delta_{j-1}^d + \mu_j^n l_{dj} \quad (36)$$

$$K_j^d = K_{j-1}^d + \theta_j^n c_{dj}^t \quad (37)$$

where $S_{d_2}^d = \Delta_{d_1}^d = K_{d_1}^d \triangleq 0$.

Particularly, the parameters $S_j^d$ and $\Delta_j^d$ may be calculated by a projection directed towards detector $d_2$, while the parameters $S_j^d$ may be calculated by a second, oppositely directed, projection. Therefore, as described below, the photon attenuation map update requires two projections along each LOR, after which the attenuation coefficient $\mu_j^{n+1}$ may be calculated by a single voxel traversal.

---

Algorithm 1 Calculation of $\mu_j^{n+1}$

1: for all voxels i do
2:    $A_i \leftarrow 0$
3:    $B_i \leftarrow 0$
4: end for
5: for all LORs d do
6:    $K \leftarrow 0$
7:    $D \leftarrow 0$
8:    for voxel i = $d_1$ + 1 : +1 : $d_2$ – 1 do
9:        $R_i \leftarrow \epsilon^{-D} K$
10:       $D \leftarrow D + \mu_j^n l_{dj}$
11:       $K \leftarrow K + \theta_i^n c_{dj}^s$
12:    end for
13:    $S \leftarrow 0$
14:    $G \leftarrow v_d - \epsilon^{-D} K$
15:    for voxel i = $d_2$ – 1 : –1 : $d_1$ + 1 do
16:       $R_i \leftarrow R_i + \theta_s^n c_{dj}^s + S$
17:       $A_i \leftarrow A_i + (1 - e^{-\mu_i^n l_{di}}) R_i$
18:       $B_i \leftarrow B_i + l_{dj} [G + (1 + \epsilon^{-\mu_i^n l_{di}}) R_i / 2]$
19:       $S \leftarrow (\theta_i^n c_{dj}^s + S) e^{-\mu_i^n l_{di}}$
20:    end for
21: end for
22: for all voxels i do
23:    $\mu_i^{n+1} \leftarrow A_i / B_i$
24: end for

---

The independence of the nth-iteration tissue activity distribution, $\theta_i^n$, and photon attenuation map, $\mu_j^n$, enables a parallel GPU based reconstruction. The speed of such reconstruction depends on its memory latency and branch divergence. Memory latency slows down the execution due to the data access time. Branch divergence serializes the, otherwise parallel, program, due to the Single-Instruction-Multiple-Data (SIMD) GPU operation principle.

A GPU based tissue activity distribution reconstruction method reduced branch divergence by processing the LORs according to their principal directions. This resulted in a balanced load distribution among GPU threads. Memory latency was reduced by caching parallel image-space slices into the GPU's shared memory. The current implementation adapts this method for the calculation of Eqs. (26)-(29).

Furthermore, in cylindrical scanners, the probability $P_i$ from Eq. (26) is fairly uniform across the field of view. Hence, for a qualitative non-attenuated tissue activity distribution reconstruction, $P_i$ could be assigned an arbitrary value, rather than calculated. However, in the presence of photon attenuation, a too small $P_i$ value would destabilize the iterative reconstruction. This would cause a divergence of the reconstructed activity values, since the terms $\gamma_{d_1 d_2}^{nd}$ in Eq. (26) are not normalized by $\theta_i''$.

Hence, in the presence of attenuation, a large enough $P_i$ value is required to stabilize the iterative reconstruction. Moreover, $P_i$ may be approximated consistently as $$P_i = \sum_d c_{di}^t$$

where the summation is over the measured LORs, rather than over all the possible LORs as in Eq. (14).

Figure 8:
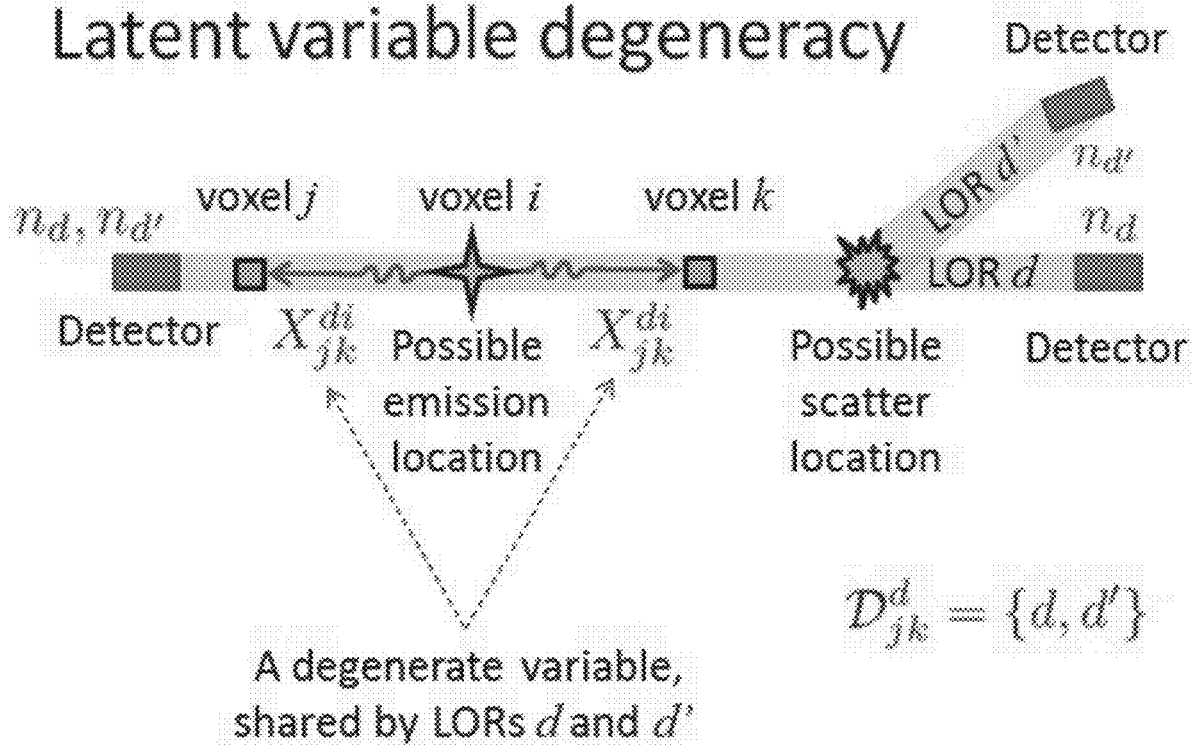
FIG. 8 shows latent variable degeneracy, where the variable $X_{jk}^{di}$ is shared by the true LOR d and by the scattered LOR $d_0$, where the degenerate LOR set $\mathcal{D}_{jk}^d$ from Eq. (38) contains the indices d and $d_0$, according to the current invention.

As shown in FIG. 8, the incorporation of scattered coincidences may create a partial overlap between some LORs. This results in a degeneracy for the variables $X_{jk}^{di}$ contained inside the overlap region. Namely, there might exist LOR sets $\mathcal{D}_{jk}^d$, such that for given voxels j and k $$\forall s \in \mathcal{D}_{jk}^d X_{jk}^{si} = X_{jk}^{di} \tag{38}$$

The reconstruction equations use the non-degenerate-, as opposed to the complete-, variable set. Practically, this requires the identification of degenerate variables, which might be computationally demanding. However, this identification might be accelerated via an approximation, which is more accurate for low scattering cross sections. This approximation assumes that all degenerate variable groups, $\mathcal{D}_{jk}^d$, contain scattered- and true-, as opposed to only scattered-, coincidences:

$$\forall \mathcal{D}_{jk}^d : \mathcal{D}_{jk}^d \backslash \text{LOS} \neq \emptyset \tag{39}$$

With this assumption, the non-degenerate reconstruction parameters are determined only by true-, as opposed to true- and scattered-, coincidences.

In some cases, notably with combined PET/MRI scanners, a priori information regarding the attenuation map is known. Such a priori information may be incorporated into the statistical model via the Maximum a Posteriori (MAP) method. When combined with the proposed statistical model, the MAP method does not couple the update equations, but rather results in an addition of a regularization term to the log-likelihood function.

Figure 9:
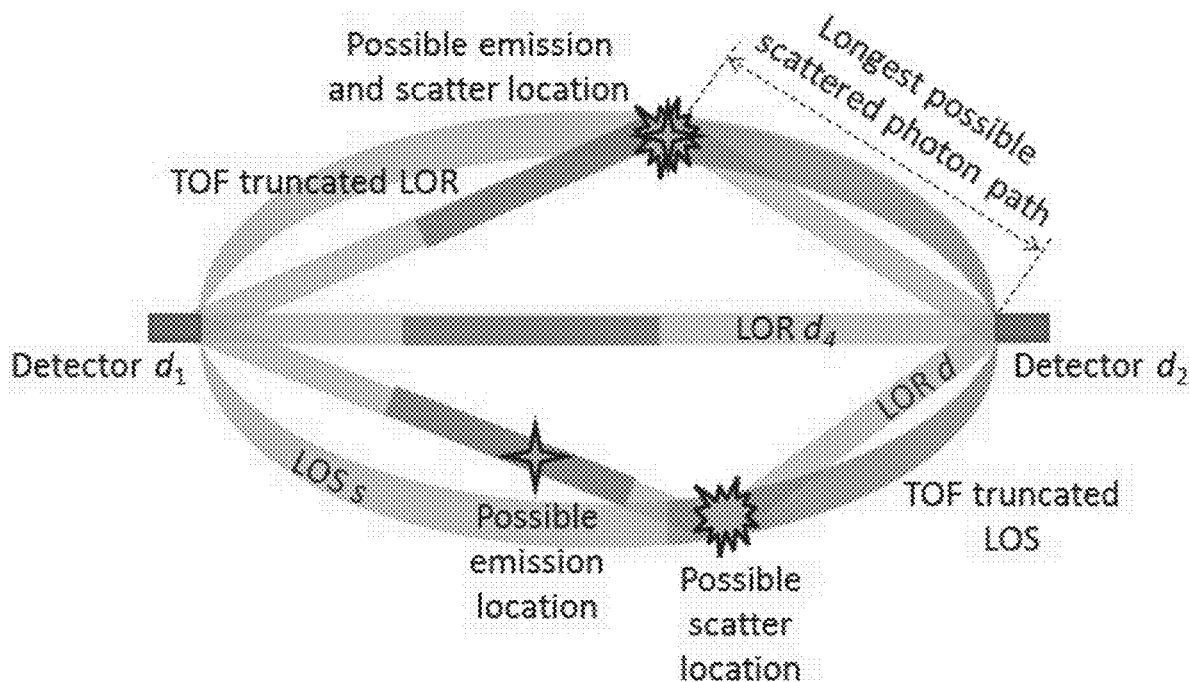
FIG. 9 shows the Time of Flight restriction of the photon emission and scatter loci, where the photon scatter loci is restricted by the longest feasible path of the detected scattered photon, which is determined by it's measured energy, according to the current invention.

Moreover, as mentioned above, TOF data may be incorporated into the statistical model via Eq. (15). This effectively restricts the emission and scatter loci, as illustrated in FIG. 9. As shown in the figure, the scatter loci restriction is possible only with scattered-, as opposed to true-, coincidences.

As described below, the incorporation of detector scatter into the statistical model, involves the coupling of LORs d and $d_4$. Such coupling is straightforward in the proposed method and was accomplished by altering the MLEM conditional probabilities. A similar approach may help generating random and scatter corrections.

With the appropriate assumptions, the current reconstruction method reduces into three other methods: A reduction into the unattenuated PET activity distribution reconstruction; A reduction into the SPECT joint activity distribution and photon attenuation map reconstruction; The CT photon attenuation map reconstruction.

The method according to the current invention uses scattered and true coincidences for joint tissue activity distribution and photon attenuation map reconstruction. It is based on a new set of latent random variables. This variable set results in a separable joint tissue activity distribution- and photon attenuation map-likelihood function, which simplifies maximization. This is the first method to result in a separable joint likelihood function for PET. The corresponding update equations have a unique solution, which may be bounded with an arbitrary precision. These equations are computationally tractable and are consistent with the PET model, the CT model and the SPECT model.

The method according to the current invention addresses detector scatter with partial energy deposition, which creates a degeneracy for the identification of tissue scattered coincidences.

Experimental error propagation is addressed via the use of Time of Flight (TOF) data (if available) and by the Single Scatter Approximation. A priori information, such as that obtained with Magnetic Resonance Imaging (MRI), may be readily incorporated into the statistical model.

Figure 10:
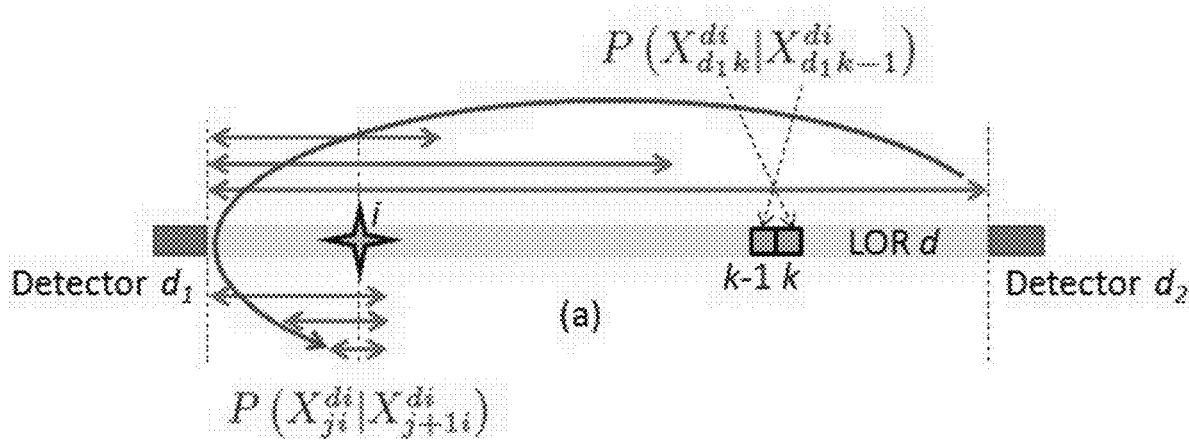
FIG. 10 shows the structure of probability function (A5), where the variables) $X_{d_1 d_2}^{di}$ are related to the observed coincidence numbers, $n_d$, via Eq. (3) and the variables $X_{ii}^{di}$ are related to the reconstructed tissue activity distribution, $\theta_i$, via Eq. (16), where the probability function in Eq. (A5) relates the variables $X_{d_1 d_2}^{di}$ and $X_{ii}^{di}$ product of conditional probabilities of the form $P(X_{ji}^{di}|X_{j+1i}^{di})$; this construction results in the introduction of a single new photon attenuation coefficient $\mu_i$ per conditional probability, according to the current invention.

Turning now to the statistical model, as mentioned above, the latent variables constitute the following subset of the complete variable set $\{X_{jk}^{di}\}$:

$$\{X_{jk}^{di} | j,k \in \mathcal{P}_{di}\} \tag{A1}$$

where, as illustrated in FIG. 10, $P_{di}$ is the set of voxel indices, j, k, such that $$\mathcal{P}_{di} = \{d_1, k \geq i\} \cup \{j > i, i\} \tag{A2}$$

The indices of each LOR increase monotonically towards detector $d_2$. As shown below, $X_{jk}^{di}$ are independent Poisson variables:

$$X_{jk}^{di} \sim \text{Pois}(\lambda_{jk}^{di}) \tag{A3}$$

where $\lambda_{jk}^{di}$ were defined in Eq. (16). Since, the latent variables completely determine the variable space via Eq. (3), $$P(X_{jk}^{di}, n) = P(X_{jk}^{di}) \tag{A4}$$

The variables $X_{jk}^{di}$ are independent for different d or i. The dependence for the same d and i arises since the number of photons cannot grow downstream (e.g. $X_{jk}^{di} \geq X_{jk+1}^{di}$). As shown in FIG. 10, the variables $X_{jk}^{di}$, for given d and i, are distributed as follows:

$$\begin{aligned} P(X_{jk}^{di})_{di} &= P(X_{d_1 d_2}^{di}, \ldots, X_{d_1 i+1}^{di}, X_{d_1 i}^{di}, \ldots, X_{ii}^{di}) \\ &= P(X_{d_1 d_2}^{di} | X_{d_1 d_2 - 1}^{di}) P(X_{d_1 d_2 - 1}^{di} \cdots) \\ &= P(X_{d_1 d_2}^{di} | X_{d_1 d_2 - 1}^{di}) \cdot \ldots \cdot P(X_{d_1 i+1}^{di} | X_{d_1 i}^{di}) \cdot \\ &\quad P(X_{d_1 i}^{di} | X_{d_1 + 1 i}^{di}) \cdot \ldots \cdot P(X_{i-1 i}^{di} | X_{ii}^{di}) \cdot \\ &\quad P(X_{ii}^{di}) \end{aligned} \tag{A5}$$

where

-continued $$X_{jk+1}^{di} \mid X_{jk}^{di} \sim Bin\left(X_{jk}^{di}, \begin{cases} e^{-\mu_i r_{dk}} & k \neq d_3 \\ 1 - e^{-\mu_{d_3} r_{dd_3}} & k = d_3 \end{cases}\right) \quad (A6)$$

$$X_{j-1k}^{di} \mid X_{jk}^{di} \sim Bin\left(X_{jk}^{di}, \begin{cases} e^{-\mu_j r_{dj}} & j \neq d_3 \\ 1 - e^{-\mu_{d_3} r_{dd_3}} & j = d_3 \end{cases}\right)$$

where the index $d_3$ was defined following Eq. (6). For voxels not adjacent to scatter locations, $d_3$, the second Binomial parameter corresponds to the probability of a photon not scattering inside an upstream voxel. For voxels adjacent to scatter locations, it corresponds to the scattering probability.

Using Eq. (A5) and the independence properties of $X_{jk}^{di}$, the likelihood function is given $$P(X_{jk}^{di}) = \prod_{\forall d} \prod_{i \in \Gamma} P(X_{jk}^{di})_{di} \quad (A7)$$

where the symbol $\forall d$ was defined following Eq. (14). Omitting the terms irrelevant for the maximization of the likelihood with respect to $\theta$ and $\mu$, the corresponding log-likelihood, $\mathcal{L}(\theta; \mu)$, is given by the following expression:

$$\mathcal{L}(\theta, \mu) = \quad (A8)$$

$$\sum_{\forall d} \sum_{i \in \Gamma_d} \left\{ -\theta_i c_{di} + X_{ii}^{di} \ln(\theta_i c_{di}) + \left[X_{d_3-1i}^{di} \ln(1 - e^{-\mu_{d_3} r_{dd_3}}) - \right.\right.$$

$$\left(X_{d_3i}^{di} - X_{d_3-1i}^{di}\right)\mu_{d_3} r_{dd_3}\right]I_{d_3 \leq i} + \left[X_{d_1 d_3+1}^{di}\right.$$

$$\ln(1 - e^{-\mu_{d_3} r_{dd_3}}) - \left(X_{d_1 d_3}^{di} - X_{d_1 d_3+1}^{di}\right)\mu_{d_3} r_{dd_3}\right]I_{d_3 > i} +$$

$$\sum_{j \in \Gamma_d} I_{j \neq d_3} \left([X_{ji}^{di} - X_{j-1i}^{di}]\ln(1 - e^{-\mu_j r_{dj}}) - X_{j-1i}^{di}\mu_j r_{dj}\right)I_{j \leq i} + $$

$$\left. \left(X_{d_1 j}^{di} - X_{d_1 j+1}^{di}\right)\ln(1 - e^{-\mu_j r_{dj}}) - X_{d_1 j+1}^{di}\mu_j r_{dj}\right]I_{j > i} \right\}$$

As mentioned in section II, the log-likelihood is maximized via the MLEM method. This method is iterative, where each iteration consists of two steps, denoted "Expectation" and "Maximization". In a given iteration n, the Expectation step calculates the form of the auxiliary function $Q(\theta, \mu \mid n; \theta^n, \mu_n)$, defined by the following expression:

$$Q(\theta, \mu \mid n; \theta^n, \mu^n) \triangleq E[\mathcal{L}(\theta, \mu) \mid n; \theta^n, \mu^n] \quad (A9)$$

The Maximization step, calculates the new parameters, $\theta^{n+1}$ and $\mu^{n+1}$, maximizing this function:

$$\{\theta^{n+1}, \mu^{n+1}\} = \underset{\theta, \mu}{\mathrm{argmax}}\, Q(\theta, \mu \mid n; \theta^n, \mu^n) \quad (A10)$$

These steps are described below.

1. Expectation Step

The auxiliary function, $Q(\theta, \mu \mid n; \theta^n, \mu_n)$, has the form of Eq. (A9), with the random variables $X_{jk}^{di}$ replaced by their conditional expectations, $$\hat{X}_{jk}^{di} \triangleq E(X_{jk}^{di} \mid n; \theta^n, \mu^n) \quad (A11)$$

As shown above, these conditional expectations are given by the following expression:

$$\hat{X}_{jk}^{di} = \theta_i^n \left\{ c_{di}^t \gamma_{jk}^{nd} + \sum_{s \in D_{jk}^d} c_{si}^t \left[ \frac{n_s}{\sum_{i' \in \Gamma_s} \theta_{i'}^n c_{si'}^t} - \gamma_{s_1 s_2}^{ns} \right] \right\} \quad (A12)$$

where the set $D_{jk}^d$ was defined following Eq. (20) and the index n denotes the previous reconstruction iteration. Note that generally, $c_{di}^t \neq c_{si}^t$, since the parameter $c_{di}^t$ might depend on the detector incidence angles of the coincidence photons. The summation in Eq. (A9) is overall-, not only the detected-, LORs. Addressing so many LORs involves a high computational load. However, this load may be reduced, assuming a low emission of photon pairs into non-detected LORs:

$$n_d = 0 \Rightarrow \forall i \in \Gamma_d, \hat{X}_{jk}^{di} \approx 0 \quad (A13)$$

This assumption is used in the rest of the paper. It is more valid for low photon attenuation values.

Turning now to the activity maximization step, setting the derivative of $Q(\theta, \nu \mid n; \theta^n, \mu^n)$, with respect to $\theta_i$ to zero, yields the following update rule for the activity parameters:

$$\theta_i^{n+1} = \frac{1}{P_i} \sum_d \hat{X}_{ii}^{di} \quad (A14)$$

where $P_i$ was defined in Eq. (14) and $\hat{X}_{ii}^{di}$ was given in Eq. (A12). In the absence of attenuation, $\mathcal{D}_{jk}^d = d$ and $\gamma_{d_1 d_2}^d = \gamma_{ii}^d = 1$. In this case, substitution of Eq. (A12) into Eq. (A14), reduces into:

$$\theta_i^{n+1} = \frac{\theta_i^n}{P_i} \sum_d \frac{n_d c_{di}^t}{\sum_{j \in \Gamma_d} \theta_j^n c_{dj}^t} \quad (A15)$$

Figure 11:
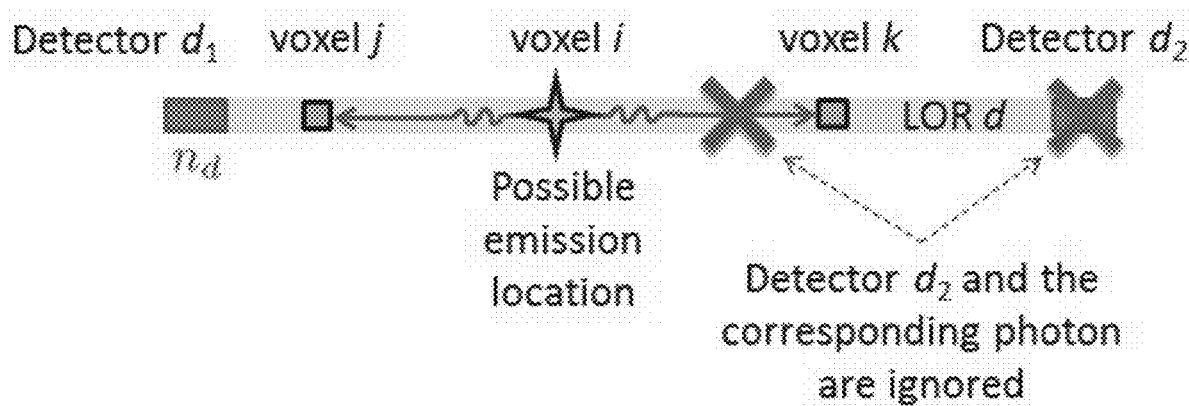
FIG. 11 shows the Reduction of PET into SPECT, where only detector $d_1$ is retained for each LOR; the photons emitted towards detector $d_2$ are ignored, reducing the random variable set in Eq. (A1) to include only the voxels between detector $d_1$ and the emission point, according to the current invention.

Regarding the attenuation maximization step, setting the derivative of $Q(\theta, \mu \mid n; \theta^n, \mu^n)$, with respect to $\mu_j$ to zero, yields Eq. (5). As shown in FIG. 11, the PET model may be reduced into a SPECT model, by retaining only detector $d_1$ in each LOR and assuming perfect collimation. In this case, the photons emitted towards detector $d_2$ may be ignored. This is equivalent to setting $I_{j \leq i} = 0$, in the calculation of $\hat{M}_j^{nd}$ and $\Delta \hat{M}_j^{nd}$.

Ignoring scattered coincidences, the activity distribution and photon attenuation map reconstruction equations are respectively reduced.

Moreover, this SPECT model may be further reduced into a CT model, by representing the CT irradiation sources by the activity inside voxels $d_2-1$. This further reduces the photon attenuation map reconstruction equation.

With respect to the derivation of condition expectations, due to the possible degeneracy in the presence of scattered coincidences, described above, a random variable $X_{jk}^{di}$ depends on the observables $$\{n_s \mid s \in \mathcal{D}_{jk}^d\} \quad (A16)$$

The conditional probability of $X_{jk}^{di}$ is given by $$P(X_{jk}^{di} \mid n) = \sum_{X_{d_1 d_2}^{di} \in X_{jk}^d} P(X_{jk}^{di} \mid X_{d_1 d_2}^{di}) P(X_{d_1 d_2}^{di} \mid n) \quad (A17)$$

where $$X_{d_1 d_2}^{di} \equiv \{X_{s_1 s_2}^{si} \mid s \in \mathcal{D}_{jk}^d\}$$

$$\mathcal{X}_{jk}^d \equiv \left\{ X_{d_1 d_2}^{di} \;\middle|\; \sum_{s \in \mathcal{D}_{jk}^d} X_{s_1 s_2}^{si} \leq X_{jk}^{di}, X_{d_1 d_2}^{di} \leq n_d \right\}$$

Hence, the conditional expectations, $\hat{X}_{jk}^{di}$, are given by $$\hat{X}_{jk}^{di} \equiv E(X_{jk}^{di} \mid n) \quad (A18)$$

$$= \sum_{X_{jk}^{di}=0}^{\infty} X_{jk}^{di} P(X_{jk}^{di} \mid n)$$

$$= \prod_{s \in \mathcal{D}_{jk}^d} \sum_{X_{s_1 s_2}^{si}=0}^{n_s} \sum_{X_{jk}^{di} = \sum_{s \in \mathcal{D}_{jk}^d} X_{s_1 s_2}^{si}}^{\infty}$$

$$\{X_{jk}^{di} P(X_{jk}^{di} \mid X_{s_1 s_2}^{si}) P(X_{s_1 s_2}^{si} \mid n)\}$$

$$= \prod_{s \in \mathcal{D}_{jk}^d} \sum_{X_{s_1 s_2}^{si}=0}^{n_s} E(X_{jk}^{di} \mid X_{s_1 s_2}^{si}) P(X_{s_1 s_2}^{si} \mid n)$$

where the last equality follows since $$P\left( X_{jk}^{di} < \sum_{s \in \mathcal{D}_{jk}^d} X_{s_1 s_2}^{si} \;\middle|\; X_{s_1 s_2}^{si} \right) = 0 \quad (A19)$$

Similarly, $$X_{d_1 d_2}^{di}, \quad (A20)$$

$$X_{jk}^{di} - \sum_{s \in \mathcal{D}_{jk}^d} X_{s_1 s_2}^{si} \mid X_{jk}^{di} \sim \text{Mult}\left( \left\{ \frac{\lambda_{s_1 s_2}^{si}}{\lambda_{jk}^{di}} \right\}_{s \in \mathcal{D}_{jk}^d}, 1 - \sum_{s \in \mathcal{D}_{jk}^d} \frac{\lambda_{s_1 s_2}^{si}}{\lambda_{jk}^{di}} \right)$$

where $$\frac{\lambda_{s_1 s_2}^{si}}{\lambda_{jk}^{di}} = \exp\left( -\sum_{i' \in \Gamma_s \setminus \Gamma_s^{jk}} \mu_{i'} l_{di'} \right) \quad (A21)$$

is the probability for a photon not scattering inside the LOR segments $\Gamma_d^{d_1 j}$ and $\Gamma_d^{k d_2}$. Since $X_{d_1 d_2}^{di}$ are independent Poisson variables, the conditional distribution of the variable $X_{jk}^{di}$ is given by $$P(X_{jk}^{di} \mid X_{d_1 d_2}^{di}) = \frac{P(X_{d_1 d_2}^{di} \mid X_{jk}^{di}) P(X_{jk}^{di})}{P(X_{d_1 d_2}^{di})} \quad (A22)$$

$$= \text{Pois}\left( \lambda_{jk}^{di} - \sum_{s \in \mathcal{D}_{jk}^d} \lambda_{s_1 s_2}^{si} \right) \mid X_{jk}^{di} - \sum_{s \in \mathcal{D}_{jk}^d} X_{s_1 s_2}^{si}$$

This implies that $$X_{jk}^{di} - \sum_{s \in \mathcal{D}_{jk}^d} X_{s_1 s_2}^{si} \mid X_{d_1 d_2}^{di} \sim \text{Pois}\left( \lambda_{jk}^{di} - \sum_{s \in \mathcal{D}_{jk}^d} \lambda_{s_1 s_2}^{si} \right)$$

Hence, the conditional expectation $E(X_{jk}^{di} \mid X_{d_1 d_2}^{di})$ is given by $$E(X_{jk}^{di} \mid X_{d_1 d_2}^{di}) = \sum_{s \in \mathcal{D}_{jk}^d} (X_{s_1 s_2}^{si} - \lambda_{s_1 s_2}^{si}) + \lambda_{jk}^{di} \quad (A23)$$

Substitution of Eq. (A23) into Eq. (A18) yields Eq. (20). Using Eq. (3), the conditional probabilities of $X_{s_1 s_2}^{si}$ are given by $$X_{s_1 s_2}^{si} \mid n_s \sim X_{s_1 s_2}^{si} \mid \sum_{j \in \Gamma_s} X_{s_1 s_2}^{sj} \sim \text{Bin}\left( n_s, \frac{\lambda_{s_1 s_2}^{si}}{\sum_{j \in \Gamma_s} \lambda_{s_1 s_2}^{sj}} \right)$$

Hence, the conditional expectation $E(X_{s_1 s_2}^{si} \mid n_s)$ is given by $$E(X_{s_1 s_2}^{si} \mid n_s) = \frac{n_s \lambda_{s_1 s_2}^{si}}{\sum_{j \in \Gamma_s} \lambda_{s_1 s_2}^{sj}} \quad (A24)$$

Finally, substitution of Eq. (A24) into Eq. (20) yields Eq. (A12). Note that since for scattered coincidences, $\Gamma_s$ overlaps several LORs, the terms $\gamma_{s_1 s_2}^s$ are not canceled out in Eq. (A24), as opposed to the true coincidence case.

Turning now to addressing the detector scattering with partial energy deposition, as mentioned above, some of the detector scatter with partial energy deposition may be filtered out during data acquisition. Thus, it can be distinguished from tissue scatter in the reconstruction of tissue activity distribution and photon attenuation map. This may be done by setting an appropriate low energy threshold, using the following considerations: according to the kinematics of Compton scatter, a photon cannot deposit more than ⅔ of its energy via a single Compton scatter inside the detector. On the other hand, a photon cannot lose more than ⅔ of its energy via a single Compton scatter inside the tissue. Hence, with detector energy resolution of $\Delta E_\xi$ KeV at photon energy $\xi$, detector scatter corresponds to detected energies, $E_{detector\ scatter}$, in the range $$0 \leq E_{\substack{detector \\ scatter}} \leq \frac{2}{3} 511 + \Delta E_{\frac{2}{3} 511} [\text{KeV}] \quad (B1)$$

and tissue scatter corresponds to detected energies, $E_{tissue\ scatter}$, in the range $$\frac{1}{3} 511 - \Delta E_{\frac{1}{3} 511} \leq E_{\substack{tissue \\ scatter}} \leq 511 [\text{KeV}] \quad (B2)$$

Figure 12:
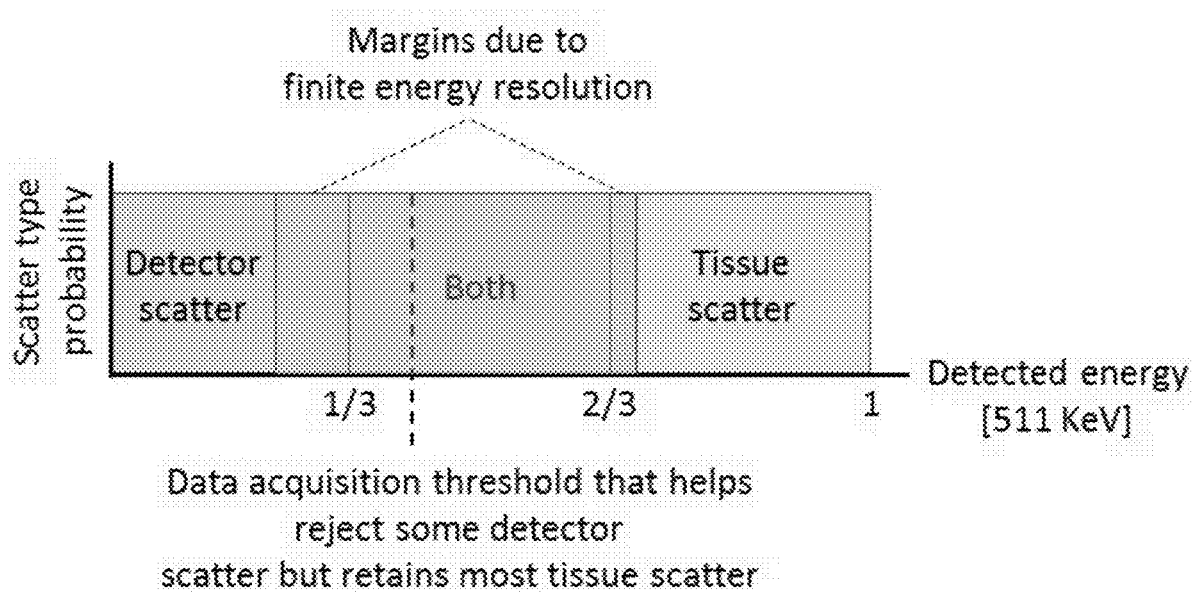
FIG. 12 shows the considerations in setting low energy data acquisition thresholds, where with detector energy resolution of $\Delta E_\xi$ KeV at photon energy $\xi$, photons with energies below ⅓(511)−$\Delta E_{1/3(511)}$ KeV indicate detector-scatter and may be discarded, where when the low energy threshold is increased above this value, the detected number of both the undesired detector-scattered and desired tissue {scattered coincidences, which are used in the reconstruction process, is reduced, according to the current invention.

Hence, as shown in FIG. 12, some of the detector scattered coincidences may be filtered out, while retaining most of the tissue scattered coincidences, by setting an appropriate low-energy data acquisition threshold. As shown in FIG. 12, this method becomes less effective as detector energy resolution decreases.

Moreover, the intra-detector scatter may be incorporated into the statistical model: let $\eta_d$ denote the number of photon pairs emitted along LOR $d_4$ (FIG. 3) and not scattered inside the tissue, such that exactly one of the two photons deposited part of its energy inside a detector.

Given the number of coincidences detected along LOR $d_4$, the conditional distribution of $\eta_d$ is given by $$\eta_d | \sum_{i \in \Gamma_{d_4}} X_{d_1 d_2}^{di} \sim \text{Bin}\left(\sum_{i \in \Gamma_{d_4}} X_{d_1 d_2}^{di}, P_d\right) \tag{B3}$$

where the probability $P_d$ was defined in the paragraph following Eq. (18). This probability may be determined experimentally or numerically by a Monte-Carlo simulation. However, it may be approximated via the known detector attenuation coefficients, $\mu d_1$ and $\mu d_2$:

$$P_d \approx e^{-\mu_{d_1} \kappa_{d_1}} + e^{-\mu_{d_1} \kappa_{d_2}} - 2e^{-(\mu_{d_1} \kappa_{d_1} + \mu_{d_2} \kappa_{d_2})} \tag{B4}$$

Since $\sum_{i \in \Gamma_{d_4}} X_{d_1 d_2}^{di}$ is a Poisson variable, $$\sum_{i \in \Gamma_{d_4}} X_{d_1 d_2}^{di} \sim \text{Pois}\left(\sum_{i \in \Gamma_{d_4}} \lambda_{d_1 d_2}^{di}\right) \tag{B5}$$

as shown below (Eq. (D6)), the variable $\eta_d$ may be treated as an independent Poisson variable:

$$\eta_d \sim \text{Pois}\left(P_d \sum_{i \in \Gamma_{d_4}} \lambda_{d_1 d_2}^{di}\right) \tag{B6}$$

Hence, detector scatter with partial energy deposition, may be incorporated into the statistical model via the following modification of the MLEM conditional expectations:

$$E(X_{d_1 d_2}^{di} | n_d) = E\left(X_{d_1 d_2}^{di} | \sum_{j \in \Gamma_d} X_{d_1 d_2}^{dj} + \eta_d\right)$$

$$= \frac{\lambda_{d_1 d_2}^{di} n_d}{\left(\sum_{j \in \Gamma_d} + P_d \sum_{j \in \Gamma_{d_4}}\right) \lambda_{d_1 d_2}^{dj}} \tag{B7}$$

As mentioned above, other effects, such as random- and undesired low-energy scatter-coincidences, may be incorporated into the statistical model via similar modifications of the conditional expectations.

Figure 13:
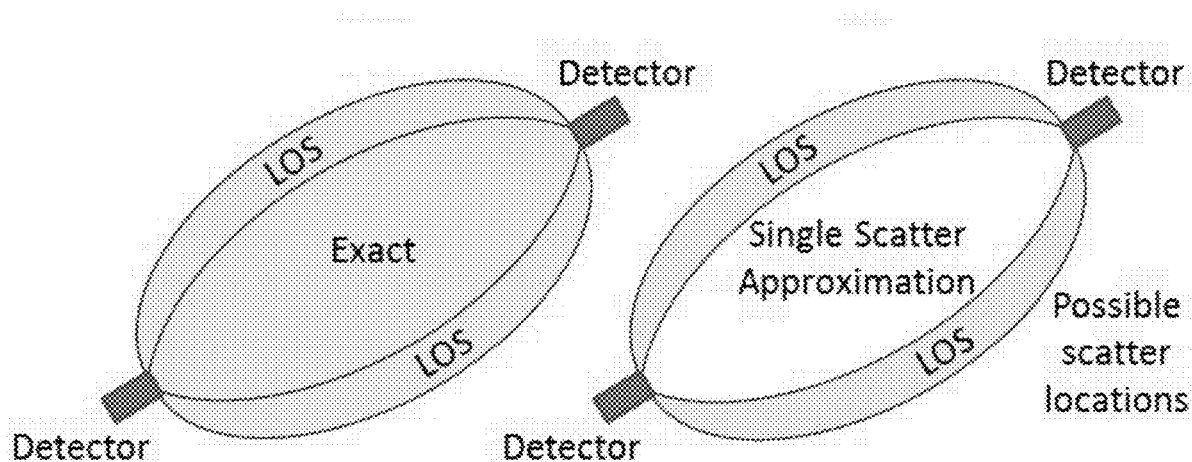
FIGS. 13*a*-13*b* show the photon attenuation coefficients affected by a given scattered coincidence; (13*a*) exact model: all the voxels bounded by the outer LOS surface are affected, (13*b*) Single Scatter Approximation: only voxels inside the LOS volume are affected, according to the current invention.

Turning now to single scatter approximation, as mentioned above, experimental error propagation may be reduced by decoupling the observables from some of the reconstructed parameters. FIG. 13a shows the photon attenuation map region affected by a given scattered coincidence. This region is comprised of the voxels bounded by the outer surface of the corresponding LOS. At small photon attenuation, assuming at most single scatter, this region may be reduced to the LOS volume, shown in FIG. 13b. This may be accomplished via the following considerations: the parameter $\gamma_{jk}^d$ is given by Eq. (18) as $$\gamma_{jk}^d = \Delta_1 - \Delta_1 \Delta_2 \tag{C1}$$

where $$\Delta_1 = 1 - e^{-\mu_{d_3} r_{dd_3}} I_{d_3 \in \Gamma_d^{jk}} \tag{C2}$$

$$\Delta_2 = 1 - e^{-\sum_{i \in \Gamma_d^{jk} \setminus d_3} \mu_i r_{d_i}}$$

Assuming small photon attenuation, both $\Delta 1$ and $\Delta 2$ are small for $d_3 \in \Gamma_d^{jk}$. Hence, the term $\Delta 1\, \Delta 2$ may be neglected in the sums over $\Gamma d$. This approximation is denoted as the Single Scatter Approximation (SSA). It implies that for tissue scattered coincidences, only one of the two photons scatters and it scatters only once. Nevertheless, according to Monte-Carlo simulations of a 511 KeV photon point source positioned inside a water cylinder, around 40% of the scattered photons scatter more than once. Hence, the SSA might not be accurate in such cases. With the SSA assumptions, each LOS contributes only the following latent variables:

$$\{X_{ii}^{di}, X_{d_1 d_2}^{di} | i \in \Gamma_d\} \tag{C3}$$

where $$\lambda_{d_1 d_2}^{di} \equiv E(X_{d_1 d_2}^{di}) = \theta_i c_{di} (1 - e^{-\mu_{d_3} r_{dd_3}}) \tag{C4}$$

$$X_{d_1 d_2}^{di} | X_{ii}^{di} \sim \text{Bin}(X_{ii}^{di}, 1 - e^{-\mu_{d_3} r_{dd_3}})$$

Hence, the photon attenuation coefficient in voxel j is affected only by the true LORs and LOS intersecting this voxel. Moreover, since in this approximation, there is no need for the calculation of the parameters $\gamma_{ji}^d$ in Eq. (29) for voxel indices i>j, the computational load is reduced, compared with the exact calculation above.

Regarding the representation of multinomial variables as independent Poisson variables, some of the dependent Multinomial variables, such as $X_{jk}^{di}$ for different LOR indices d, but the same voxel index i, are treated as independent Poisson variables. This may be justified by consider the Multinomial vector r, with the parameters n and p, where $n \equiv \Sigma_i r_i$ is a Poisson variable:

$$r \sim \text{Mult}(n, p)$$

$$n \sim \text{Pois}(N) \tag{D1}$$

The total probability of r is given by $$P(r) = P(r|n)P(n) = \left(\frac{n!}{\Pi_i r_i!} \prod_i p_i^{r_i}\right) \frac{e^{-N} N^n}{n!} \tag{D2}$$

Since $n = \Sigma_i r_i$ and $\Sigma_i p_i = 1$, this expression simplifies to $$P(r) = \prod_i \frac{e^{-(p_i N)} (p_i N)^{r_i}}{r_i!} \tag{D3}$$

A further summation over r\r$_i$ yields:

$$r_i \sim \text{Pois}(p_i N) \quad \text{(D4)}$$

Hence, r$_i$ are independent Poisson variables. Particularly, a Binomial variable r, with a Poisson parameter n, $$r \sim \text{Bin}(n,p)$$

$$n \sim \text{Pois}(n) \quad \text{D5}$$

may be treated as a Poisson variable with the mean pN:

$$r \sim \text{Pois}(pN) \quad \text{(D6)}$$

To see this, evaluate $P(r) = \Sigma_n P(r|n) P(n)$.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. All such variations are considered to be within the scope and spirit of the present invention as defined by the following claims and their legal equivalents.

What is claimed:

1. A method for joint reconstruction of tissue activity distribution and photon attenuation map in positron emission tomography (PET), the method comprising:
    a. obtaining from a PET scanner both true-coincidence observation data and scattered-coincidence observation data; and
    b. jointly reconstructing both the tissue activity distribution and the photon attenuation map from both the true-coincidence observation data and the scattered-coincidence observation data;
    wherein jointly reconstructing both the tissue activity distribution and the photon attenuation map comprises implementing by a computer a maximum likelihood expectation maximization (MLEM) method that maximizes the PET likelihood function using an iterative maximization of an additively separable joint tissue activity-attenuation surrogate function derived from a statistical model of PET coincidence observation events;
    wherein the statistical model contains observed variables representing both the true-coincidence observation data and the scattered-coincidence observation data;
    wherein the statistical model contains latent random variables parameterized by voxel-pair indices along each PET line of response, where each of the latent random variables represents a number of photon pairs reaching two voxels on opposite sides of a possible emission location voxel.

2. A method for joint reconstruction of tissue activity distribution and photon attenuation map in positron emission tomography (PET), the method comprising:
    a. obtaining from a PET scanner both true-coincidence observation data and scattered-coincidence observation data; and
    b. jointly reconstructing both the tissue activity distribution and the photon attenuation map from both the true-coincidence observation data and the scattered-coincidence observation data;
    wherein jointly reconstructing both the tissue activity distribution and the photon attenuation map comprises implementing by a computer a maximum likelihood expectation maximization (MLEM) method that maximizes the PET likelihood function using an iterative maximization of an additively separable joint tissue activity-attenuation surrogate function derived from a statistical model of PET coincidence observation events.

* * * * *